US008591433B2

(12) United States Patent
Elberling

(10) Patent No.: US 8,591,433 B2
(45) Date of Patent: Nov. 26, 2013

(54) METHOD TO DESIGN ACOUSTIC STIMULI IN THE SPECTRAL DOMAIN FOR THE RECORDING OF AUDITORY STEADY-STATE RESPONSES (ASSR)

(75) Inventor: Claus Elberling, Smørum (DK)

(73) Assignee: Maico Diagnostic GmbH, Berlin (DE)

( * ) Notice: Subject to any disclaimer, the term of this patent is extended or adjusted under 35 U.S.C. 154(b) by 523 days.

(21) Appl. No.: 11/630,392

(22) PCT Filed: Jun. 30, 2005

(86) PCT No.: PCT/EP2005/053093
§ 371 (c)(1),
(2), (4) Date: Apr. 2, 2007

(87) PCT Pub. No.: WO2006/003172
PCT Pub. Date: Jan. 12, 2006

(65) Prior Publication Data
US 2008/0033317 A1 Feb. 7, 2008

(30) Foreign Application Priority Data
Jul. 2, 2004 (EP) .................................. 04388046

(51) Int. Cl.
*A61B 5/00* (2006.01)
(52) U.S. Cl.
USPC .............................................. 600/559
(58) Field of Classification Search
USPC ............ 600/544, 559, 378; 128/920; 73/585
See application file for complete search history.

(56) References Cited

U.S. PATENT DOCUMENTS

| 6,123,677 A * | 9/2000 | Heitmann et al. ............ 600/559 |
| 6,524,258 B1 | 2/2003 | Sturzebecher et al. |
| 2001/0049480 A1 | 12/2001 | John et al. |

OTHER PUBLICATIONS

B. Ross et al., "Frequency Specificity of 40 Hz Auditory Steady-State Responses" in Hearing Research, vol. 186, No. 1-2, Dec. 2003, pp. 57-68.
S. Griffiths et al., "The Amplitude Modulation-Following Response as an Audiometric Tool," Ear and Hearing, vol. 12, No. 4, 1999, pp. 235-241.
Dolphin, W.F., "The Envelope Following Response to Multiple Tone Pair Stimuli," Hearing Research, 110 (1997) pp. 1-14.
Hall, J.W., "Auditory Brainstem Frequency Following Responses to Waveform Envelope Periodicity," Science, 205, Sep. 1979, pp. 1297-1299.
Smith, et al., "Human Auditory Frequency-Following Responses to a Missing Fundamental," Science, 201, Aug. 1978, pp. 639-641.

* cited by examiner

*Primary Examiner* — Brian Szmal
(74) *Attorney, Agent, or Firm* — Dykema Gossett PLLC

(57) ABSTRACT

The invention relates to a method to design and generate frequency-specific electrical or acoustical stimuli for the recording of auditory steady-state responses, ASSR, from human individuals, where the stimuli are generated as a combination of a series of three or more spectral components (i.e. pure tones), each having a specified frequency, amplitude and phase and where the frequency difference between the successive pure tones in the series preferably is constant=$f_s$. The invention further relates to a device for detection of ASSR and to a software program for use in such device.

4 Claims, 12 Drawing Sheets

METHOD TO DESIGN ACOUSTIC STIMULI IN THE SPECTRAL DOMAIN FOR THE RECORDING OF AUDITORY STEADY-STATE RESPONSES (ASSR)

AREA OF THE INVENTION

The present invention relates to the field of recording Auditory Evoked Responses (AER) from human test subjects and especially of obtaining evoked responses that originate from specific places or frequency areas along the auditory pathway. The invention concerns a spectral domain design of acoustic stimuli especially for the recording of Auditory Steady-State Responses (ASSR).

BACKGROUND OF THE INVENTION

A series of AER-tests relate to the field of objective hearing tests which particularly are used with infants and small children, since early in life standard pure-tone audiometry, which demands active participation of the individual test subject, is not yet possible.

Several of the known test methods that record evoked responses from the auditory pathway make use of broad band click stimuli. Since a click stimulus excites a relatively broad frequency area, it is difficult to obtain frequency specific information by such stimulus. Never-the-less, click stimuli are employed in many clinical test setups especially for otoneurological evaluations or when it is the purpose of the testing to obtain a general impression about the hearing acuity of the individual. This latter applies for instance to new born hearing screening programs. However, for a more detailed analysis of the individual hearing acuity, like for instance in audiological diagnostic evaluations, frequency specific information is in demand, especially to establish a basis for an appropriate (re)habilitation by hearing aids, cochlear implants or the like.

To this end, a series of relatively new test methods have matured. These methods are referred to as Auditory Steady-State Responses (ASSR) or by other acronyms. For a review of the ASSR—the reader is referred to e.g. Picton et al. 2003. ASSR-procedures make use of a sustained stimulus often produced as a continuous carrier waveform consisting of a single or a plurality of pure tones, a broad band or a band limited noise or the like, which is modulated either in amplitude, in frequency or in both, by specific modulation signals.

Most of the electrophysiological activity which underlies the generation of auditory evoked responses (AER) is caused by non-linear processes in individual nerve fibers, neurons or other neural units, and the AER are therefore related to the envelope of the acoustic stimulus. This is especially true for the ASSR, which consequently is composed of a combination of the fundamental frequency and its harmonics of the modulation signal. Thus, the ASSR is most readily detected and analyzed in the spectral domain rather than in the temporal domain, (Picton et al. 2003).

ASSR-stimuli have hitherto been described and defined in the temporal domain, as modulation (in amplitude, frequency or in both) of one or multiple carriers. However, several ways of designing an appropriate stimulus for an ASSR-test are described in the literature (e.g. Sturzebecher et al. 2001, John et al. 2003, Picton et al. 2003) and several patents apply to this problem. In the experimental animal 'beat' stimuli generated by pairs of pure tones have also been used—e.g. Dolphin, 1997.

One patent by Sturtzebecher et al. 2000 (U.S. Pat. No. 6,524,258) deals with the use of several amplitude modulated carriers having a frequency that is offset by a specific frequency difference, and where all carriers are modulated with the same modulation signal.

Another patent by John et al. 2001 deals with a broad spectrum of problems related to the recording of ASSR. Relevant to the problem described herein, the John et al. patent especially concerns the use of stimuli that may be modulated independently in amplitude and in frequency or a signal whose envelope is modulated by an exponential modulation signal—see also John et al. 2002.

It is a basic characteristic of an auditory evoked response that the magnitude of the response depends on the number of auditory units that are activated synchronously by the stimulus. This is part of the reason why a click stimulus, which simultaneously activates a broad band of frequencies, provides evoked responses that in general are larger than those obtained by narrow band or frequency specific stimuli (Eggermont, 1977).

However, in the peripheral part of the auditory pathway, the Cochlea, all frequency areas along the cochlear partition do not get excited simultaneously because of the travel time through the cochlea—from the base (high frequency area) to the apex (low frequency area) (Elberling, 1974). This has lead to the design of so-called chirp stimulus (e.g. Dau et al. 2000) where the individual frequency components of the click are time-adjusted to compensate for the cochlea travel time, so the responses from nerve fibers from different parts of the cochlear partition get time-aligned or synchronized. It was demonstrated that the chirp-stimulus generates Auditory Brainstem Responses (ABR) with larger amplitudes than those generated by the corresponding standard click stimulus.

A similar approach was used by Don et al. 1997 who demonstrated that if prior to summation, narrow-band Auditory Brainstem Responses, (ABR)—that originate from different frequency regions along the cochlear partition—are time-aligned to compensate for the individual cochlea delay, this would create a much larger stacked ABR than the broad band ABR.

In the clinic, it is important to keep test time at a minimum for the detection of an auditory response or to obtain a specific response quality. Larger response amplitudes will in general result in shorter test time, and the compensation for cochlear travel time could therefore be one way of increasing response amplitude and thereby shortening the test time.

A general problem in the recording of auditory evoked responses is how to avoid that stimulus related artifacts (being either electromagnetic or acoustic) are introduced in the recording path and here cause an interaction with the physiological response. Traditionally these problems have been minimized or eliminated by careful considerations and counter measures in the recording set-up and the proper use of shielded acoustical transducers. However, at high stimulus levels it is not always possible to get rid of the artifact.

For auditory evoked responses that are recorded using brief acoustic stimuli it is possible to use the time lag between the stimulus and the generation of the evoked response and to introduce a recording time window which only incorporates the evoked response and leaves out the stimulus artifact.

Another way which traditionally has been used is to change the polarity of every other stimulus; a method which eliminates the artifact through the averaging process which most often is applied as a means to improve the signal-to-noise ratio in order to recognize the tiny evoked responses that are buried in the physiological background noise.

For the ASSR where both stimulus and response are continuous temporal separation between stimulus artifact and response is not possible. As described above, the ASSR is readily analyzed in the frequency domain, since the response energy is located only at the fundamental frequency of the stimulus envelope (the repetition or modulation frequency) and its harmonics. Most of the ASSR energy is contained within the first six harmonics or so (Cebeulla et al. 2004), which for a repetition frequency of 100 Hz will cover the frequency range up to about 600 Hz. For an ASSR stimulus that for instance consists of a single pure tone carrier which is amplitude modulated with a low frequency pure tone the stimulus energy (and that of the artifact) will be located around the carrier frequency. For lower modulation frequencies (Gower than e.g. 100 Hz) and higher stimulus carrier frequencies (larger than e.g. 1000 Hz) the energy of the response and artifact will be spectrally separated unless frequency-aliasing occurs—like that described by e.g. Picton & John, 2004. However, for lower stimulus frequencies (e.g. 500 Hz) possible interaction between response and artifact may occur—not only covering the same spectral area but actually sharing the same frequency bins in the response spectrum.

SUMMARY OF THE INVENTION

It is the objective of the present invention to provide a new way of designing and generating an appropriate ASSR-stimulus that enhances the response from the test subject.

According to the invention this is done by using a spectral domain approach, This design enables the stimulus - and the frequency area it effectively stimulates - to be spectrally precisely defined. Through the spectral domain approach the stimulus is generated - not by modulation - but by combination, e.g., summation, of a number of continuous pure tones, each having individual amplitude and phase and a frequency precisely defined at the frequency axis. The frequency region that gets stimulated - corresponding to a narrower or wider response area - can be accurately defined through this design method.

In one embodiment the frequency difference between the successive pure tones in the series is constant, fs.

In another embodiment the individual pure tone has a frequency that is an integer multiple of the constant frequency difference, fs.

In another embodiment the individual pure tone has a frequency that corresponds to a half-integer multiple of the constant frequency.

In another embodiment the individual pure tone has a phase (i.e., time-lag), that compensates for the corresponding cochlear delay or any other phase or temporal deviations in the stimulus system, the recording system and/or in the auditory pathway. Hereby the response from the test subject is enhanced.

In another embodiment the combination is formed as the sum, the average or the like of the three or more spectral components.

In another embodiment the electrical or acoustical stimuli is generated in software or in hardware.

The invention further relates to a device for detecting ASSR. Such device does according to the invention comprise means for generating stimulin, means for providing the stimuli to a test subject and means for detecting responses to the stimuli from the test subject. The device may, except for the means for generating stimuli, be of a type known in the art.

Preferably the device comprises a software program for providing the stimuli.

The invention also relates to a software program for use in a device as described above. The program comprises program code for generating components program code combining the components and program code for providing a combined output to be supplied to a test subject as a stimuli.

Preferably the program comprises code for giving the individual pure tone a phase (i.e. time-lag), that compensates for the corresponding cochlear delay or any other phase or temporal deviations in the stimulus system, the recording system and/or in the auditory pathway. Hereby the response from the test subject is enhanced.

The program is preferably stored on a readable storage media, such as a diskette, a CD-ROM, a DVD, a disk drive, a flash memory or a similar memory.

The invention will be described in more detail in the following description of preferred embodiments, with reference to the drawings.

DESCRIPTION OF PREFERRED EMBODIMENTS

Figure 1:
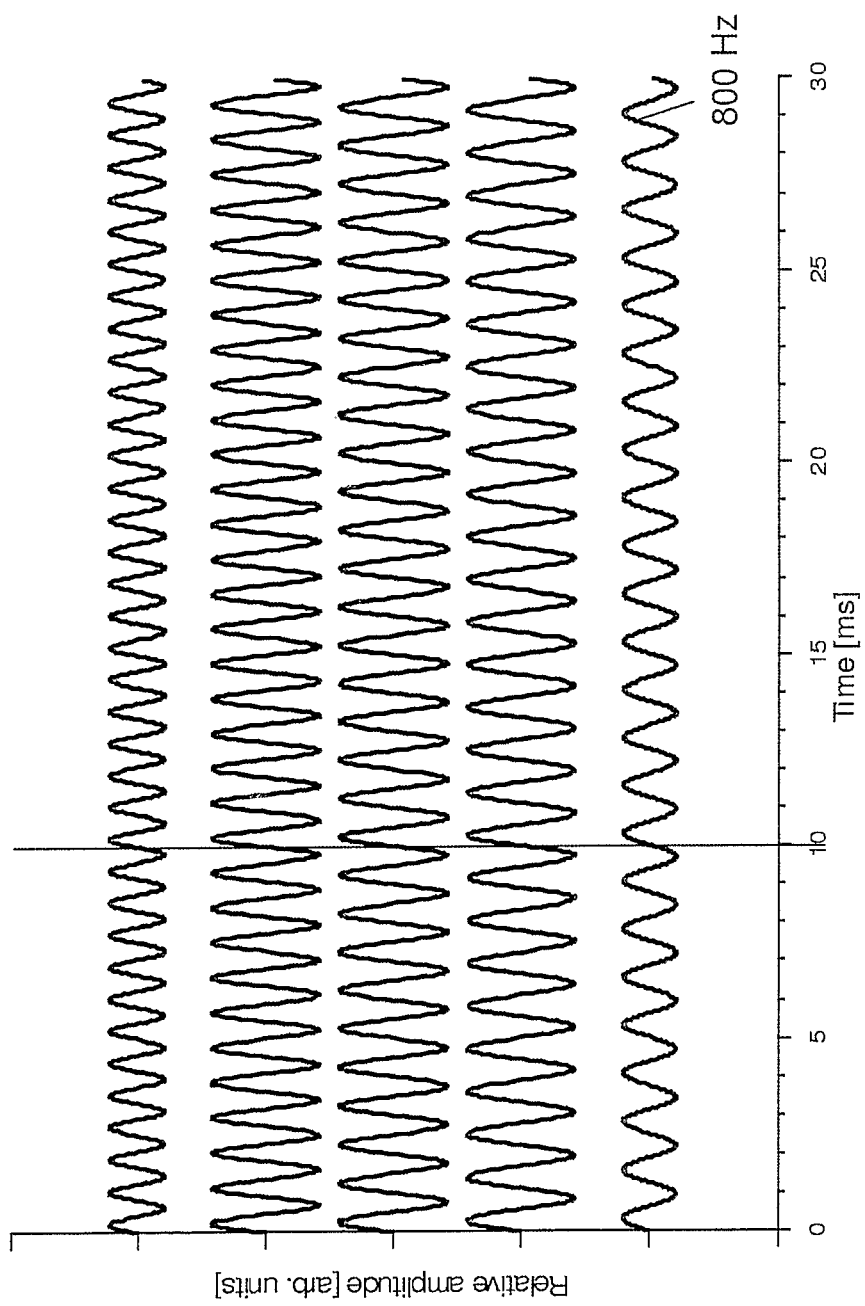
FIG. 1 Shows an example with five pure tones having the frequencies 800, 900, 1000, 1100 and 1200 Hz. The frequency difference is 100 Hz and each frequency corresponds to an integer multiple of this difference. The tones with the lowest and highest frequency have half the amplitude than that of the other three pure tones and all the pure tones (sinusoidal waveforms) have the same starting phase.
Figure 2:
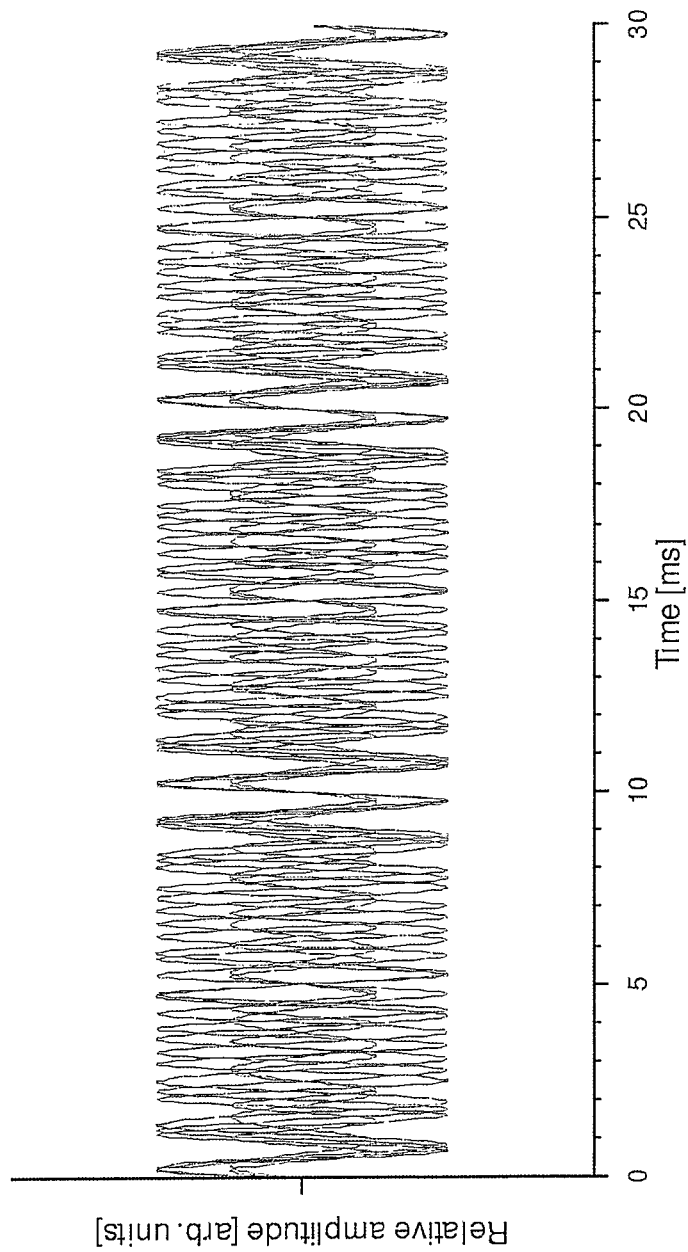
FIG. 2 Shows the pure tones in FIG. 1 plotted on top of each other and demonstrates that with a repetition frequency that corresponds to the frequency difference, $f_s$=100 Hz, all five pure tones become in-phase (viz. every 10 ms).
Figure 3:
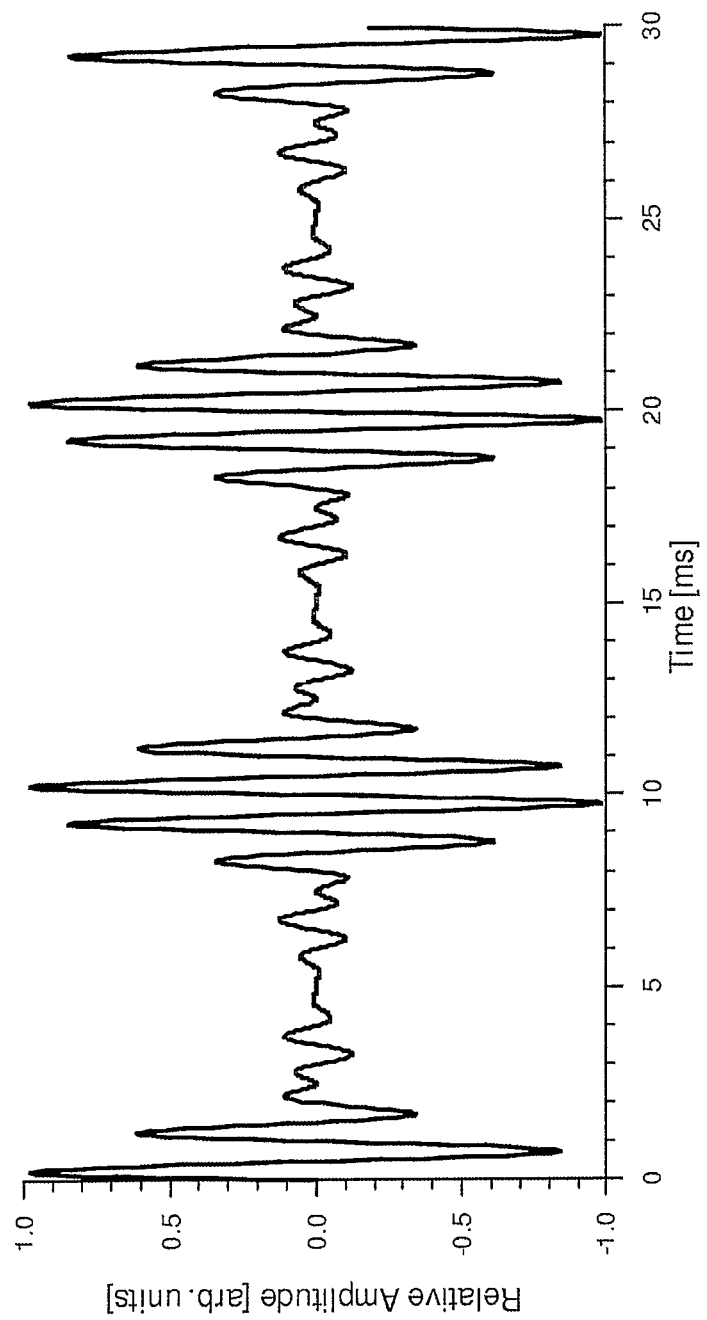
FIG. 3 Shows the final stimulus comprised by the pure tones in FIG. 1. The final stimulus is here the average of the five pure tones.

As an example, such a stimulus could be generated by five pure tones with the frequencies corresponding to 800, 900, 1000, 1100 and 1200 Hz. In this example, the tones with the lowest and highest frequency have half the amplitude than that of the other three tones and all tones (sinusoidal waveforms) have the same starting phase. The corresponding five pure tones are shown in FIG. 1. In this example the frequency difference between the pure tones is constant (=100 Hz) and the central spectral component has a frequency (=1000 Hz) that is an integer of the frequency difference (=10*100 Hz). The five pure tones are plotted on top of each other in FIG. 2, and the figure demonstrates that with a repetition frequency that corresponds to the frequency difference (viz. 100 Hz) all five pure tones become in-phase (viz. every 10 ms). This repetition frequency is some times referred to as the 'beat'-frequency. The final stimulus—which is the sum (or the mean) of the five pure tones—is plotted in FIG. 3, and has some similarities to a carrier frequency that is modulated by a complex window function.

With a classical amplitude modulation approach the periodicity of the final stimulus waveform is defined by the characteristics of the modulation signal. Contrary to this, the periodicity of the final stimulus waveform that is designed via the spectral approach (or the summation approach) would be given—as a first order approximation—by the spacing between the individual frequency components. For example, if the stimulus consists of n spectral components (n=three or more, uneven numbers) with a spacing of $f_s$ [Hz], then the frequency area that is covered by the stimulus would correspond to $(n-1)*f_s$ [Hz] placed around the central spectral component, and the temporal periodicity would correspond to $t_s=1/f_s$ [s]. It can further be demonstrated that the temporal envelope of the final stimulus corresponds to a window function with a complexity, which depends on the exact parameter values (the number, frequencies, amplitudes and phases). Such a window function could for instance be described as a special Blackman-Harris window (Harris, 1978).

With a stimulus designed through the spectral domain approach, each individual spectral components of the ASSR-stimulus could be given a time alignment (or phase adjustment) that compensates for the corresponding cochlear delay. This would result in a stimulus, which would produce larger response amplitudes than those obtained with a corresponding stimulus without such compensation. Preliminary test results have in fact been able to demonstrate this.

Figure 4:
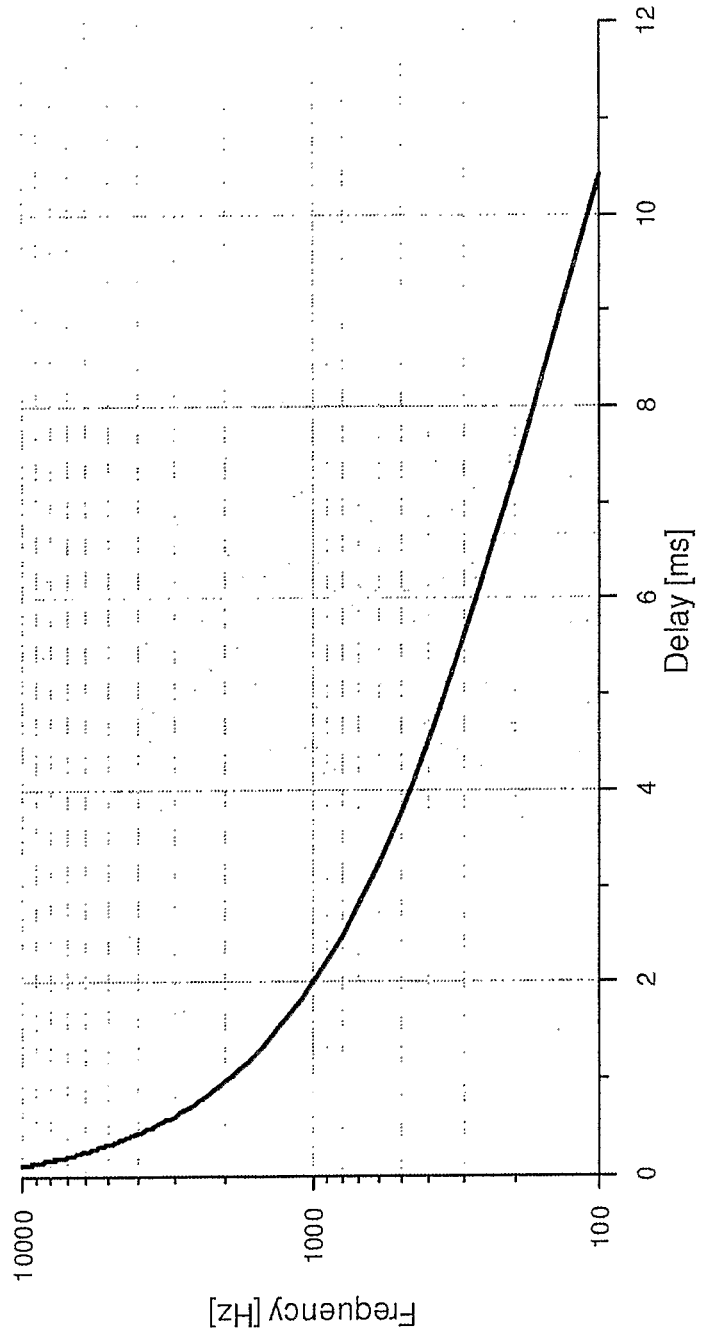
FIG. 4 Shows a model of the Cochlear delay based on data from de Boer (1980) and Greenwood (1990).
Figure 5:
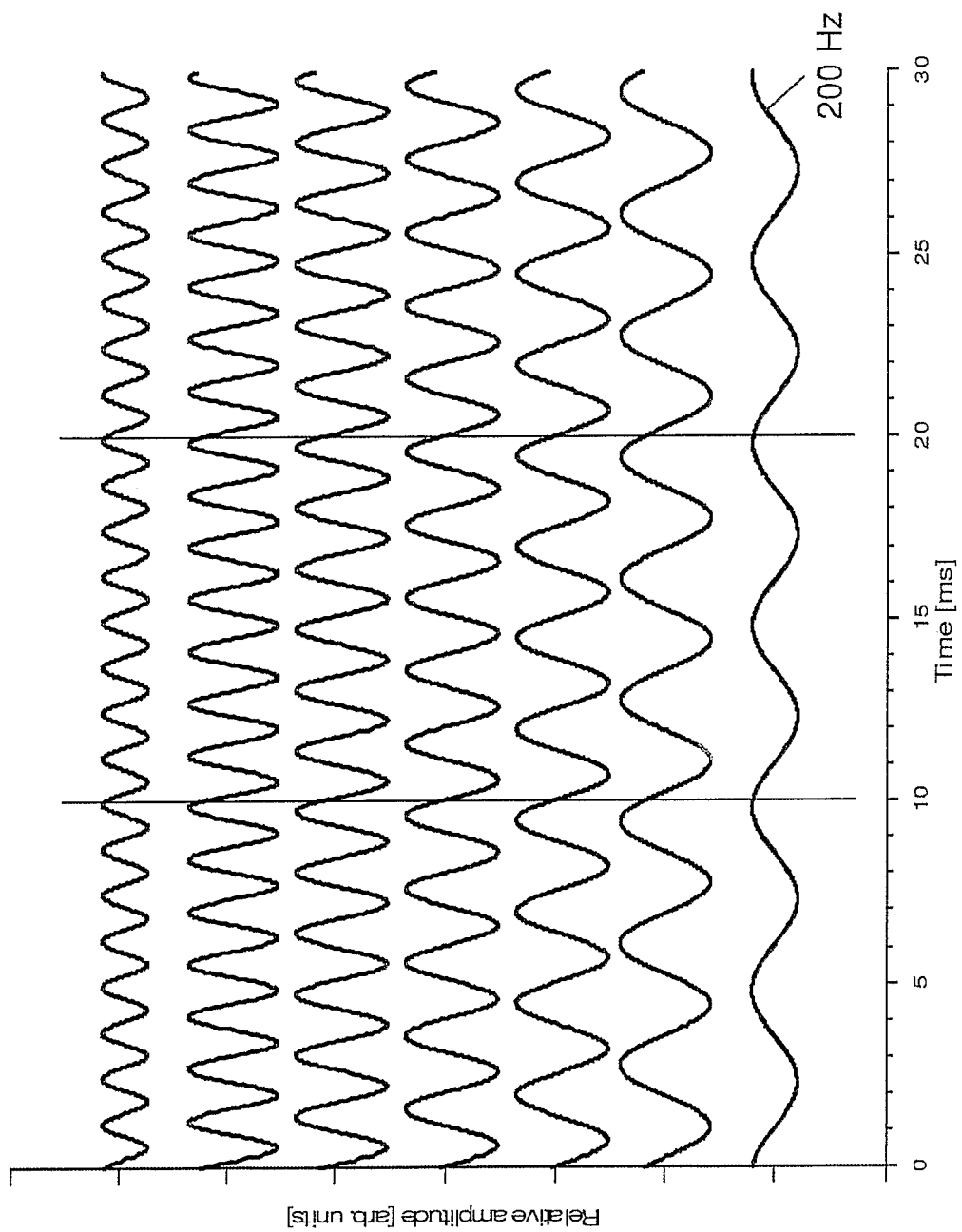
FIG. 5 Shows an example with seven pure tones having the frequencies 200, 300, 400, 500, 600, 700 and 800 Hz. The tones with the lowest and highest frequency have half the amplitude than that of the other five pure tones and all pure tones (sinusoidal waveforms) have a time-lag, which compensates for its cochlear delay according to the data in FIG. 4 relative to the delay at 100 Hz.
Figure 6:
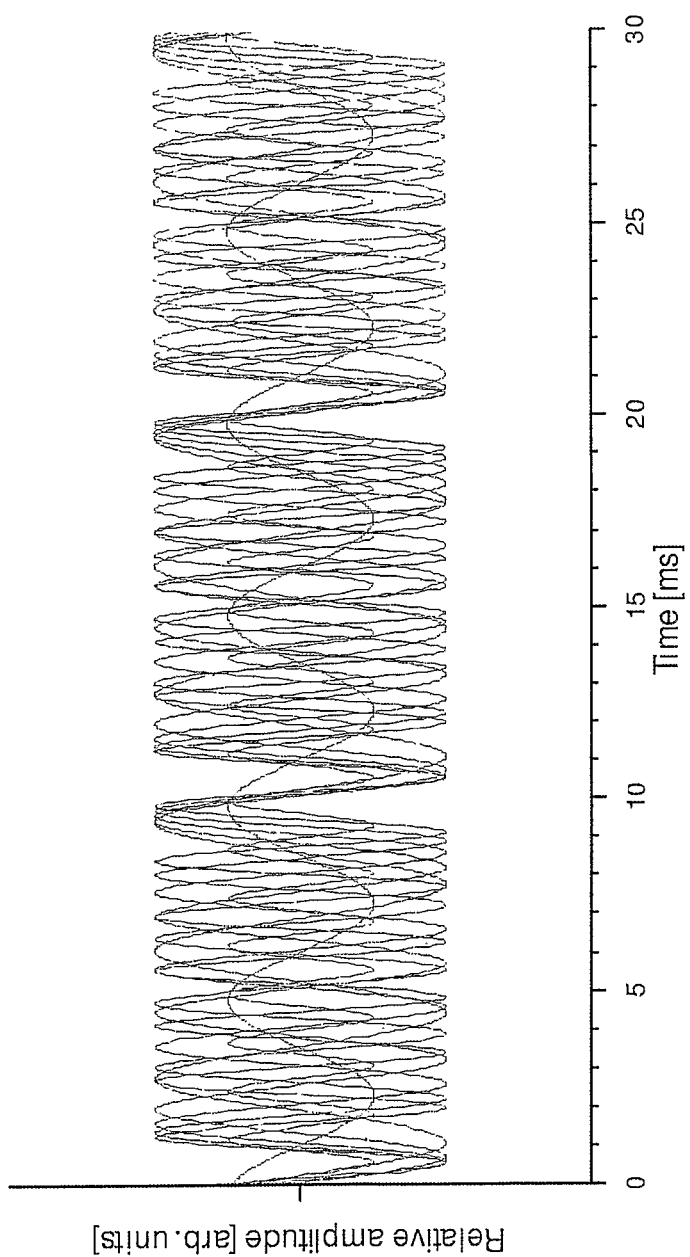
FIG. 6 Shows the pure tones in FIG. 5 plotted on top of each other.
Figure 7:
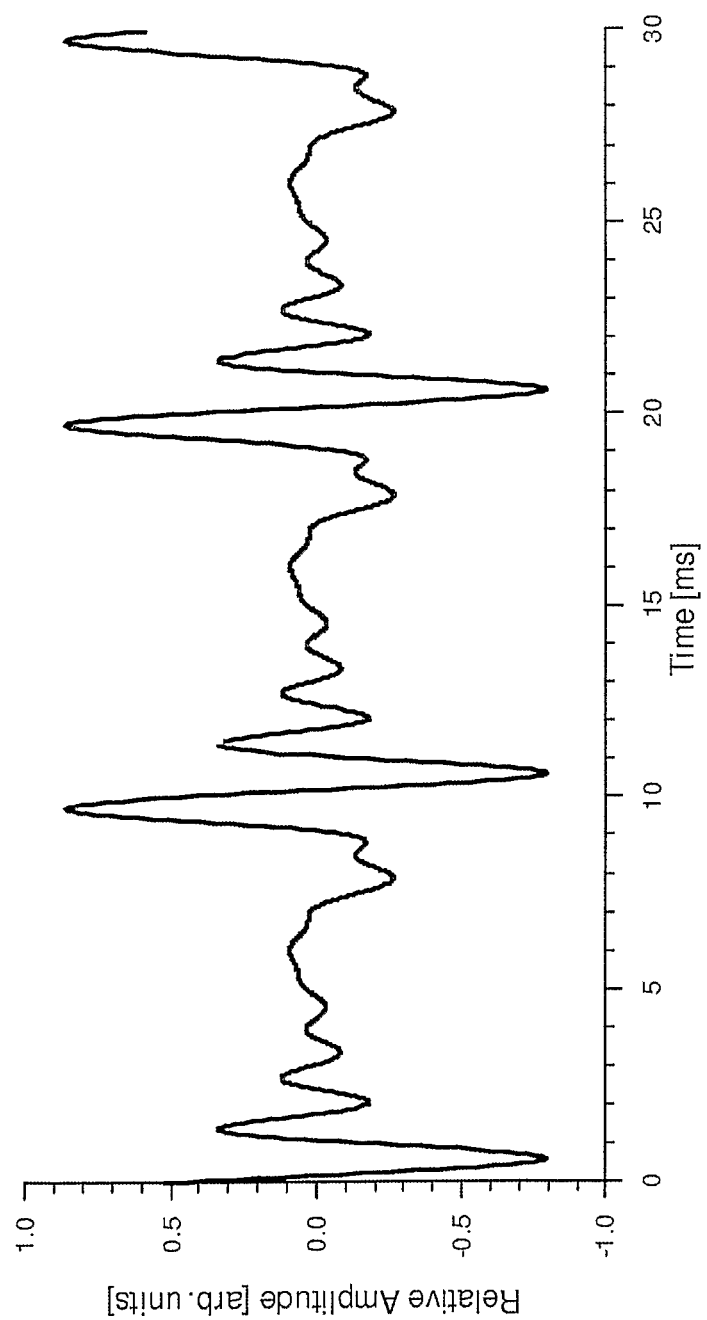
FIG. 7 Shows the final stimulus comprised by the pure tones in FIG. 5. The final stimulus is here the average of the seven pure tones. Due to the introduced time-lag the resulting 'time-pulse' now appears with a left-right asymmetry.

As an example, such a stimulus could be generated by seven pure tones with the frequencies corresponding to 200, 300, 400, 500, 600, 700 and 800 Hz. In this example, the tones with the lowest and highest frequency have half the amplitude than that of the other five tones and each pure tone is given a time-lag which compensates for its cochlear delay. This delay can be estimated from a cochlear model—for instance as the one shown in FIG. 4 that is based on de Boer (1980) and Greenwood (1990). The time-lagged pure tones are shown in FIG. 5, and are plotted on top of each other in FIG. 6. The final stimulus—which is the sum (or the mean) of the five pure tones—is plotted in FIG. 7. Due to the introduced time-lag the resulting 'time-pulse' now appears with a left-right asymmetry.

By the spectral design approach (or summation approach) some response-artifact problems can be avoided especially for low frequency stimuli. This is obtained by allowing the individual pure tones to be located at frequencies that not are integer values of the constant frequency difference between the different spectral components.

Figure 8:
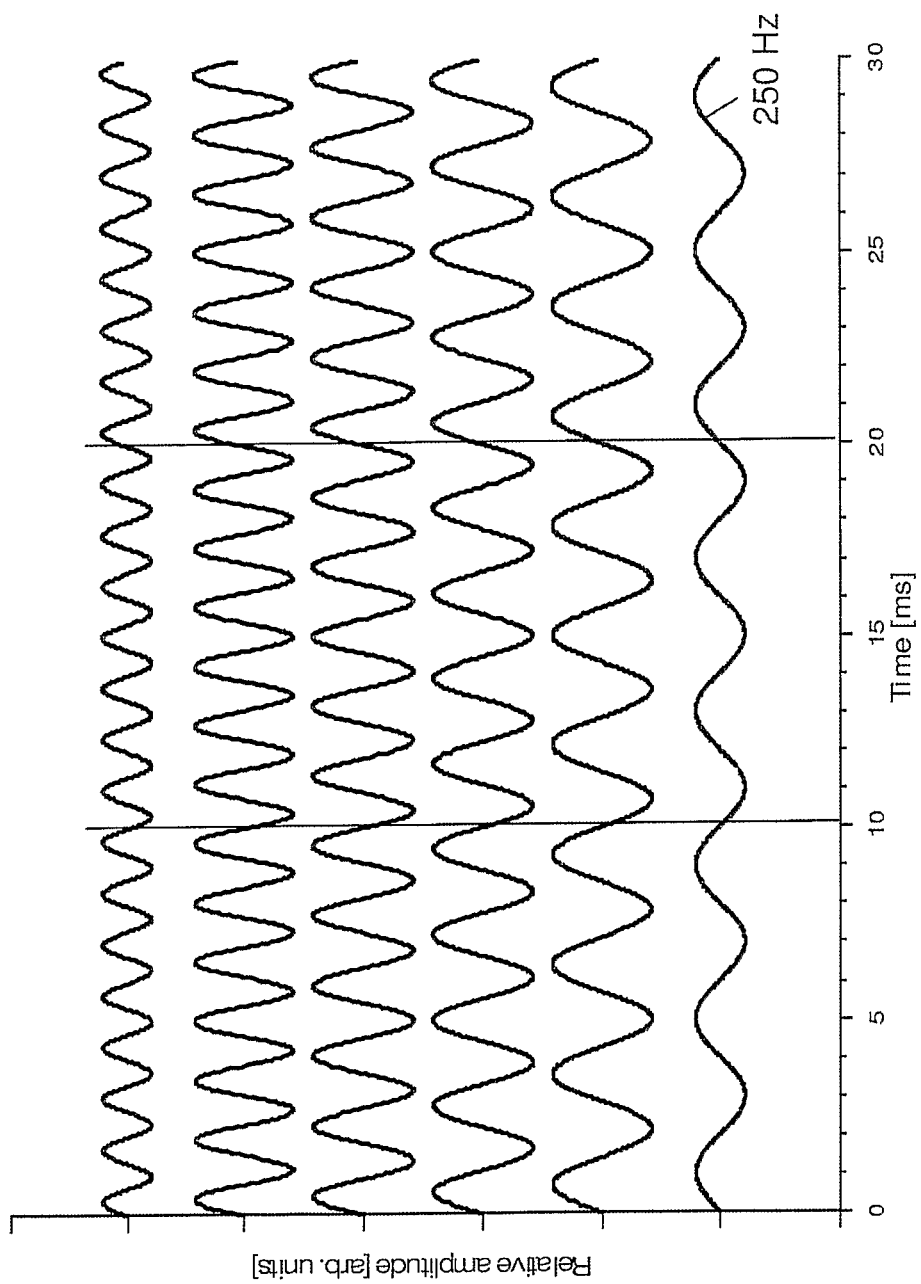
FIG. 8 Shows an example with six pure tones having the frequencies 250, 350, 450, 550, 650 and 750 Hz. The frequency difference is 100 Hz and each frequency corresponds to a half-integer multiple of this difference. The tones with the lowest and highest frequency have half the amplitude than that of the other four pure tones and all the pure tones (sinusoidal waveforms) have the same starting phase.
Figure 9:
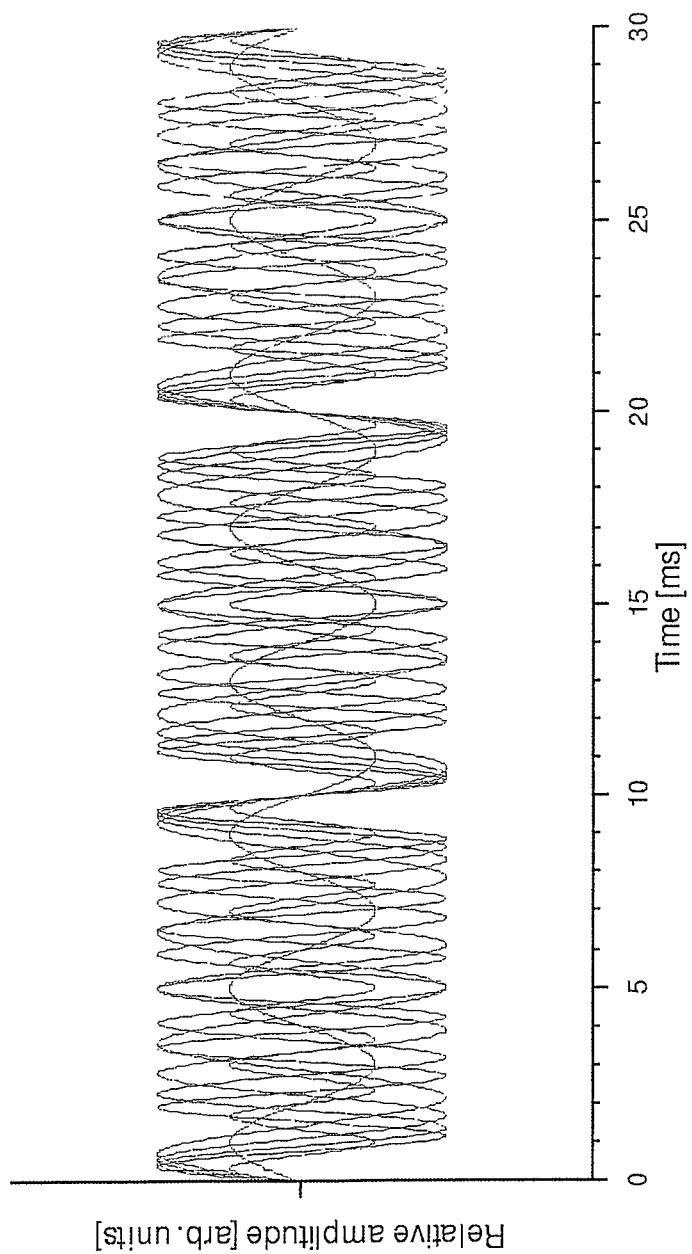
FIG. 9 Shows the pure tones in FIG. 8 plotted on top of each other.
Figure 10:
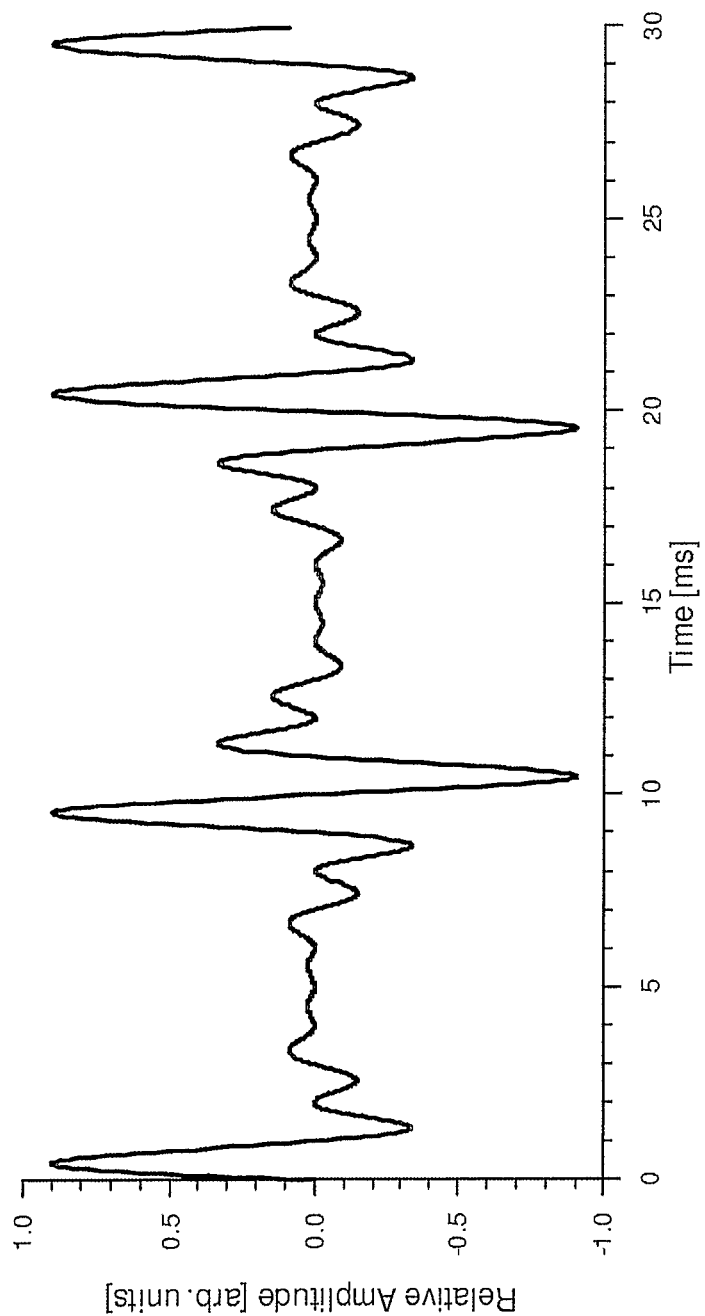
FIG. 10 Shows the final stimulus comprised by the pure tones in FIG. 8. The final stimulus is here the average of the six pure tones. Since the frequencies are located at half-integer multiples of the frequency difference, $f_s$, the final stimulus demonstrates polarity-inversion from period to period.
Figure 11:
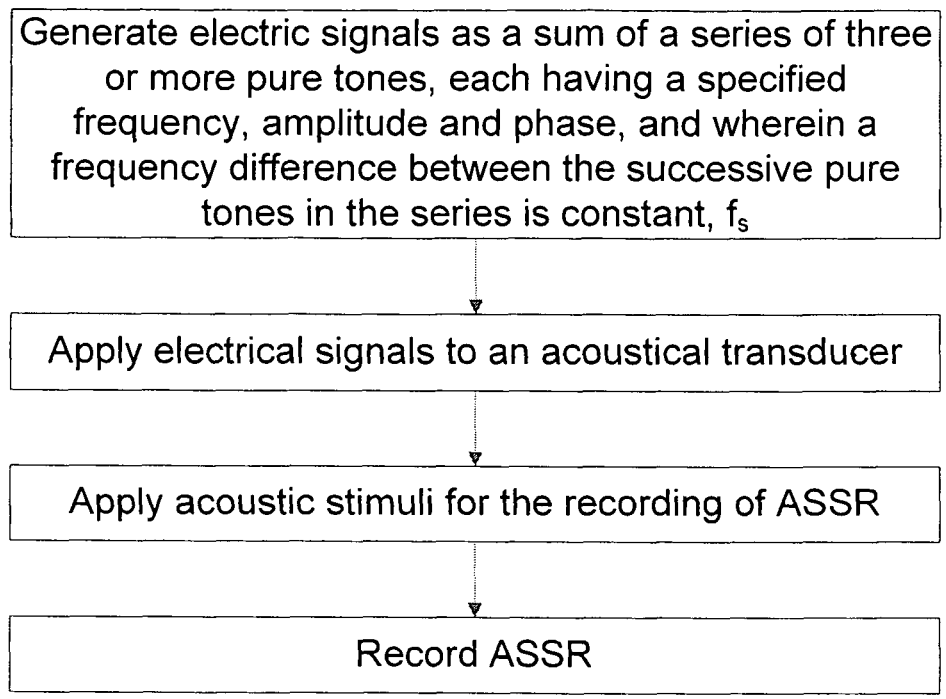
FIG. 11 illustrates the method of the invention.
Figure 12:
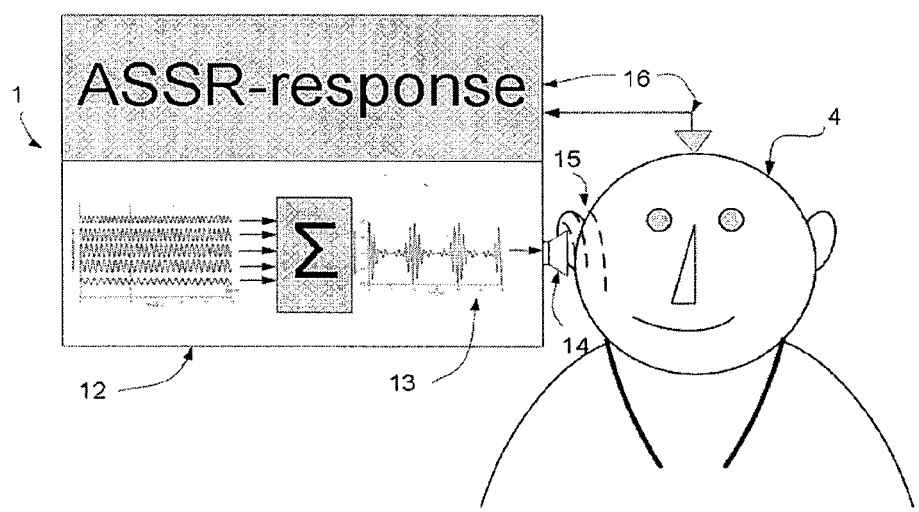
FIG. 12 depicts an apparatus for accomplishing the method of the invention.

Following the example in FIG. 1, such a stimulus could for instance be generated by six pure tones with equal amplitude and phase and with the frequencies corresponding to 250, 350, 450, 550, 650 and 750 Hz. The tones with the lowest and highest frequency have half the amplitude than that of the other four tones and all tones (sinusoidal waveforms) have the same starting phase as shown in FIG. 8. As before, the frequency difference between the pure tones is constant (=100 Hz) but now the spectral components have frequencies that do not correspond to integer multiples of the frequency difference. The six pure tones are plotted on top of each other in FIG. 9 and the figure demonstrates—as before—that with a repetition frequency that corresponds to the frequency difference (viz. 100 Hz~10 ms) all six pure tones appear in-phase. The final stimulus is plotted in FIG. 10, and because the pure tones in this example are located half-way between integer values of the frequency difference, the temporal waveform demonstrates polarity-inversion from period to period. This corresponds to the polarity change of brief stimuli that was mentioned previously. If the frequencies of the pure tones were not exactly located half-way between the integer values of the frequency difference, the temporal waveform of the resulting stimulus would have the same envelope but a rolling phase from period to period. In any case, the spectrum of the final stimulus will only have components at the used pure tone frequencies and therefore, will not share any frequency bins with the evoked response.

LIST OF REFERENCES

Dau, T., Wegner, O., Melleret, V. and Kollmeier, B. 'Auditory brainstem responses with optimized chirp signals compensating basilar-membrane dispersion'. J. Acoust. Soc. Am. 107, 1530-40. 2000.

Cebulla, M., Stürzebecher, E. and Elberling, C. 'Objective detection of auditory steady-state response: Comparison of one-sample and q-sample tests'. Presented at: "The International Conference on Newborn Hearing Screening, Diagnosis and Intervention". Cernobbio, Italy. 2004.

de Boer, E. 'Auditory physics. Physical principles in hearing theory I'. Phys. Rep. 62, 87-174. 1980.

Dolphin, W. F. 'The envelope following response to multiple tone pair stimuli. Hear. Res. 110, 1-14. 1997.

Don, M., Masuda, A., Nelson, R. and Brackmann, D. 'Successful detection of small acoustic tumors using the stacked derived-band auditory brain stem response amplitude. Am. J. Otol. 18, 608-21. 1997.

Eggermont, J. J. 'Electrocochleography'. In: Keidel & Neff (eds.), Handbook of Sensory Physiology, V: Auditory System, 3: Clinical and Special Topics, pp 625-705. Springer-Verlag, Berlin. 1977.

Elberling, C. 'Action potentials along the cochlear partition recorded from the ear canal in man'. Scand. Audiol. 3, 13-9. 1974.

Greenwood, D. D. 'A cochlear frequency position function for several species—29 years later'. J. Acoust. Soc. Am. 87, 2592-2605. 1990.

Harris, F. J. 'On the use of windows for harmonic analysis with the discrete Fourier transform'. Proc. I.E.E.E., 66, 1, 51-83. 1978.

John, M. S., Dimitrijevic, A. and Picton, T. W. 'Efficient stimuli for evoking auditory steady-state responses'. Ear & Hear., 24, 5, 406-423. 2003.

John, M. S., Dimitrijevic, A. and Picton, T. W. 'Auditory steady-state responses to exponential modulation envelopes'. Ear & Hear., 23, 2, 106-117. 2002.

John, M. S. and Picton, T. W. 'System and method for objective evaluation of hearing using auditory steady-state responses'. U.S. Pat. No. 6,602,202.

Picton, T. W., John, M. S., Dimitrijevic, A. and Purcell, D. 'Human auditory steady-state responses'. Int. J. Audiol. 42, 4, 177-219. 2003.

Picton, T. W. and John, M. S. 'Avoiding electromagnetic artifacts when recording auditory steady-state responses'. J.A.A.A. in press. 2004.

Stürzebecher E., Cebulla, M. and Pschirrer, U. 'Efficient stimuli for recording of the amplitude modulation following response'. Audiology, 40, 63-68. 2001

Stürzebecher, E., Cebulla, M., Baagh, M. and Thie, R. 'Method for an objective frequency-specific determination of an audible threshold value using an amplitude modulation following response (AMFR)'. U.S. Pat. No. 6,524,258.

The invention claimed is:

1. A method of recording Auditory Evoked Responses (AER) from human test subjects comprising:
   (a) designing and generating frequency-specific electrical signals as a sum of a series of three or more pure tones, each pure tone having individual frequency, amplitude and phase, and wherein a frequency difference, $f_s$, between the successive pure tones in the series is constant,
   (b) applying said signals to an acoustical transducer to provide corresponding acoustic stimuli,
   (c) applying said acoustic stimuli for the recording of AER from a human, and
   (d) recording the AER.

2. The method according to claim 1, wherein an individual pure tone has a frequency that is an integer multiple of the frequency difference, $f_s$.

3. The method according to claim 1, wherein an individual pure tone has a frequency that corresponds to a half-integer multiple of the frequency difference, $f_s$.

4. The method according to claim 1, wherein an individual pure tone has a phase that compensates for corresponding cochlear delay or any other phase or temporal deviations in at least one of a stimulus system, a recording system, and in an auditory pathway.

* * * * *

UNITED STATES PATENT AND TRADEMARK OFFICE
CERTIFICATE OF CORRECTION

PATENT NO. : 8,591,433 B2  
APPLICATION NO. : 11/630392  
DATED : November 26, 2013  
INVENTOR(S) : Claus Elberling Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 652 days.

Signed and Sealed this
Twenty-second Day of September, 2015

Michelle K. Lee
*Director of the United States Patent and Trademark Office*